United States Patent [19]

Plum et al.

[11] 4,374,778

[45] Feb. 22, 1983

[54] MONOALKYLFLUOROTIN COMPOUNDS

[75] Inventors: Hans Plum, Hamm; Ulrich Schroeer, Kamen-Methler, both of Fed. Rep. of Germany

[73] Assignee: Schering Aktiengesellschaft, Berlin and Bergkamen, Fed. Rep. of Germany

[21] Appl. No.: 280,300

[22] Filed: Jul. 6, 1981

[30] Foreign Application Priority Data

Aug. 1, 1980 [DE] Fed. Rep. of Germany ....... 3029174

[51] Int. Cl.³ .............................................. C07F 7/22
[52] U.S. Cl. .................................. 260/429.7; 252/8.6
[58] Field of Search ...................................... 260/429.7

[56] References Cited

U.S. PATENT DOCUMENTS 3,493,592  2/1970  Shapiro et al. ................... 260/429.7
4,191,698  3/1980  Gitlitz et al. ..................... 260/429.7
4,254,046  3/1981  Franz et al. ...................... 260/429.7

OTHER PUBLICATIONS

Sawyer, Organotin Compounds, Marcel Dekker, Inc. N.Y. V1, pp. 200–205, 213 & 214 (1971).

*Primary Examiner*—Helen M. S. Sneed
*Attorney, Agent, or Firm*—Curtis, Morris & Safford

[57] ABSTRACT

What are disclosed are monoalkylfluorotin compounds of the formula

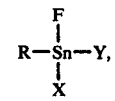

wherein R is alkyl having 1 to 12 carbon atoms, X taken alone is fluorine or carboxylate, Y taken alone is chlorine, carboxylate, or

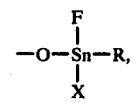

or wherein X and Y, taken together, are oxygen, and methods for making said compounds from alkanestannonic acids.

9 Claims, No Drawings

MONOALKYLFLUOROTIN COMPOUNDS

The present invention relates to certain monoalkylfluorotin compounds and to methods of making the same. Such monoalkylfluorotin compounds are suitable for hydrophobizing textiles and mineral surfaces.

A first feature of the present invention are monoalkylfluorotin compounds of the general formula

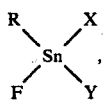

in which compounds R is alkyl having from 1 to 12 carbon atoms, X taken alone is fluorine or carboxylate, Y taken alone is chlorine, carboxylate, or the group

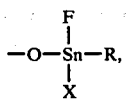

or wherein X and Y taken together are oxygen, and wherein Y is preferably

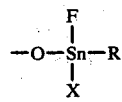

and X is fluorine. The carboxylate group X can be derived from mono-, di-, or higher poly-acids which may be aliphatic or aromatic in nature and is not critical to the synthesis or properties of the compound in which it is present. Preferred carboxylate groups are derived from mono-acids free of possibly interfering substituents, preferably mono-acids of aliphatic hydrocarbons having from 1 to 12 carbon atoms, or of aromatic hydrocarbons, including araliphatic hydrocarbons, preferably those having a phenyl nucleus such as benzoic acid or the phthalic acids. Compounds in which the alkyl group R is butyl or octyl are also preferred.

A further feature of the invention is a method for the preparation of stannoxane compounds of the aforementioned formula wherein Y is

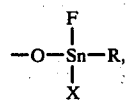

which method involves the reaction of the corresponding alkanestannonic acid with hydrogen fluoride in a molar ratio of at least 1:2 at a temperature from 20° C. to 100° C.

A further feature of the invention is a method for the preparation of monoalkylfluorotin compounds of the aforementioned formula wherein X is fluorine and Y is carboxylate, in which method stannoxane compounds, such as those prepared by the method described immediately above, are reacted with an excess of a carboxylic acid at a temperature from 70° C. to 120° C. and the water of reaction is then removed.

A further feature of the invention is a method for making monoalkyldifluorotin monocarboxylates by the direct reaction of a corresponding stannonic acid, hydrogen fluoride, and a carboxylic acid in a mol ratio of 1:2:1 at a temperature from 70° C. to 120° C., removing the water of reaction.

Still another feature of the invention is a method for making monoalkylfluorotin dicarboxylates by the direct reaction of a corresponding stannonic acid, hydrogen fluoride, and a carboxylic acid in a mol ratio of 1:1:2 at a temperature from 70° C. to 120° C., removing the water of reaction.

A further feature of the invention is a method for the preparation of compounds of the aforementioned formula wherein X and Y taken together are oxygen, which method involves the reaction of the corresponding alkanestannonic acid with hydrogen fluoride in a molar ratio of 1:1 at a temperature from 20° C. to 100° C.

A further feature of the invention is a method for the preparation of compounds of the aforementioned formula wherein X is fluorine and Y is chlorine by the reaction of the corresponding alkyltin trichloride with an aqueous solution of an alkali metal fluoride in a mol ratio of 1:2 at a temperature from 80° C. to 100° C.

The aforementioned compounds are represented as monomers for the sake of clarity. In fact, as is known, they can form polymeric structures depending on the substituents present on tin, particularly in the case of organotin-oxygen compounds and organotin-fluorine compounds [cf. W. P. Neumann, "Die Organische Chemie des Zinns", ("The Organic Chemistry of Tin"), Ferd.-Enke-Verlag, Stuttgart, 1967, pages 13 and 134.]

Further, depending on the alkyl group, stannoxanes may be present in equilibrium with the corresponding hydroxides (cf. the considerations affecting the equilibrium between hydroxides and stannoxanes, for example in W. P. Neumann, op. cit.)

The substances according to the invention can be used for hydrophobizing, including, for instance, textile finishing and the treatment of mineral surfaces, for example in buildings. The compounds according to the invention have considerable advantages over the tin compounds heretofore used in the art. Thus, the fluorine bound in the molecule effects considerably improved adhesion to mineral surfaces; in textile finishing, improved adhesion is achieved by way of hydrogen bonding to fluorine.

As substrate materials which can be provided with a hydrophobizing finish, sandstone and gas concrete are particularly suitable, as well as concrete and asbestos cement.

When the compounds of the present invention are used at high temperatures, the content of undesirable hydrochloric acid in the pyrolysis gases is reduced or completely suppressed in comparison with chlorotin compounds. Since, in pyrolytic applications, fluorine for the main part remains on the mineral surface, only a very small amount of hydrofluoric acid is set free. This acts on iron-containing materials to passivate them, so that high corrosion damage of the sort which occurs with hydrochloric acid is not to be expected. Further, the hydrofluoric acid in the waste gases can be readily removed quantitatively by simple precipitation reactions, for example with lime.

It is possible to obtain the compounds of the present invention in solution. Further, however, they have very good properties if they are handled as solids. As loose powders, they do not show the undesired property of clumping together.

In contrast to the use of a monoalkyltin compound not containing fluorine, together with a separate fluorine compound, only a single compound according to the invention needs to be measured and, in this way, a constant ratio of elements is always present also.

Since in many of the following Examples, the decomposition temperature of the compounds is surprisingly lower than, for example, that of dibutyltin difluoride, the possibility is presented of reducing the pyrolysis temperature in pyrolytic applications. It is further a very great advantage that, in pyrolysis, considerably smaller amounts of material escape than is the case for diorganotin compounds. At a heating rate of 10° C. per minute between room temperature and 500° C., for example, about a 20 percent smaller loss by weight is measured for bis-(monobutyldifluoro)-stannoxane as compared with dibutyltin difluoride, and about a 15 percent smaller loss by weight is measured in the case of bis-(monooctyldifluoro)-stannoxane.

The compounds of the invention can be used per se or in admixture with auxiliaries. For example, the solids may be admixed with such materials as favorably influence free-flowability, such as aerosils. Also, the compounds may be complexed with other fluorides such as $NH_4F$, $KF$, or $SbF_3$.

A better understanding of the present invention and of its many advantages will be had by referring to the following specific Examples, given by way of illustration. Alkanestannonic acids, used as starting materials in some syntheses, are known in the art. Their preparation is described in "Organotin Compounds", by A. K. Sawyer, Volume 1, pages 213–215, Marcel Dekker, New York 1971, for instance.

EXAMPLE 1

Bis-(monobutyldifluoro)-stannoxane 208.7 g (1 mol) of butanestannonic acid are introduced into 40 g (2 mol) of hydrofluoric acid, present as a 20 percent solution in water. After the exothermic reaction has terminated, the mixture is reacted for a further 2 hours at 80°–90° C. and then filtered. The vacuum filtered product is dried at 60° C. and 80 mm Hg to constant weight.

Yield: 91 percent. The missing amount of tin can be precipitated from the solution with excess NaOH as butylstannonic acid.

Analysis (weight percent): Sn=51.99 (theory=53.5); F=15.3 (theory=17.1).

Melting Point: 203°–206° C.

EXAMPLE 2

Bis-(mono-n-octyldifluoro)-stannoxane 79.48 g (0.3 mol) of octanestannonic acid are introduced into 30 g of a 40 percent solution of HF in 100 ml of water (0.6 mol HF) with stirring and the mixture is stirred for an additional 2 hours at 80° C. After further dilution with 50 ml of water, the solid is filtered off and the precipitate is dried.

Yield: 85 g (quantitative).

Analysis (percent by weight): Sn=41.8 (42.7); F=12.9 (13.7).

Melting point: 200° C.

EXAMPLE 3

Bis-(mono-n-octyldifluoro)-stannoxane

In a variation of Example 2, a large excess of HF (6 mols of HF per mol of octanestannonic acid) is used. The material is worked up as in Example 2.

When, as here, the alkanestannonic acid starting material has a relatively long alkyl chain, reaction nevertheless stops with formation of the corresponding insoluble bis-(alkyldifluoro)-stannoxane despite the use of an excess of HF. In contrast, if butanestannonic acid is reacted with HF present in excess of a 2:1 molar ratio, unidentifiable water-soluble products are obtained. For this reason, the ratio of HF to alkanestannonic acid is kept at 2:1 when lower alkyl groups are involved: as the alkyl chain length increases, the ratio of HF to alkanestannonic acid may also be increased, if this offers any advantage.

The yields are almost quantitative.

Analysis (percent by weight): Sn=41.4 (42.7); F=13.0 (13.7).

EXAMPLE 4

Difluoro-monooctyltin chloride 33.8 g (0.1 mol) of octyltin trichloride are dissolved in 10 ml of acetone and introduced into a solution of 12 g (0.206 mol) of KF in 100 ml of water. A precipitate forms immediately. After removal of the acetone at a bath temperature of 80° C., the solid is filtered and dried.

Yield: 30.2 g (99.3 percent of theory).

Analysis (percent by weight): Sn=37.7 (38.9); F=11.1 (12.5); Cl=9.6 (11.6).

On long heating of the suspension, the chloride content of the product falls off noticeably.

EXAMPLE 5

Monobutylfluorotin oxide 20.87 g (0.1 mol) of butanestannonic acid and 2 g (0.1 mol) of HF, introduced as a 40 percent solution, are combined. The mixture is diluted with water to an extent that it remains stirrable and is heated at 80° C. for 2 hours. The mixture is then filtered and the solid product dried.

Yield: 21 g (quantitative).

Analysis (percent by weight): Sn=56.0 (56.3); F=8.2 (9.0).

EXAMPLE 6

Monooctyldifluorotin acetate 55.6 g (0.1 mol) of bis-(mono-n-octyldifluoro)-stannoxane are heated to boiling with 10.2 g (0.1 mol) of acetic acid anhydride in 120 g of acetic acid. Everything dissolves to form a clear solution. The acetic acid is distilled off and a viscous mass of 64.5 g (98 percent yield) remains.

The same final product is also obtained with less acetic acid: however, a completely clear solution is not obtained during the reaction.

Solubility: 55 g in 100 g of boiling acetic acid.

Analysis (percent by weight): Sn=35.3 (36.11); F=10.8 (11.56).

During reaction, acetyl fluoride escapes when excess acetic acid anhydride is present.

EXAMPLE 7

Monobutyldifluorotin acetate 48.90 g (0.11 mol) of bis-(monobutyldifluoro)-stannoxane are treated with 10.2 g (0.1 mol) of acetic acid anhydride as in Example 6.

Yield: 52 g (95 percent of theory) of a hard solid.
Solubility: 65 g in 100 g of boiling acetic acid.
Analysis (percent by weight): Sn=42.3 (43.53); F=12.4 (13.9).

Melting region: Begins to melt at 80° C. and is molten at 117° C.

EXAMPLE 8

Monoisopropylfluorotin diacetate 19.47 g (0.1 mol) of isopropanestannonic acid are combined with 10 g of 20 percent hydrofluoric acid (0.1 mol) and heated to 80° C. after the addition of 13.2 g (0.22 mol) of acetic acid. Water and excess acetic acid are distilled off by the application of a vacuum, leaving a light yellow residue in an amount of 28.67 g (96 percent of the theoretical yield).

Analysis (percent by weight): Sn=39.9 (39.7); F=6.16 (6.36).

The compound is water soluble.

EXAMPLE 9

Didodecyldifluorodiacetoxystannoxane 32 g (0.1 mol) of dodecanestannonic acid, 5 g of 40 percent HF (0.1 mol) and 6 g (0.1 mol) of acetic acid are combined in 50 ml of toluene and the water of reaction is removed azeotropically. Subsequently, the excess toluene is completely removed in vacuum. A residue of 37.4 g (100 percent of the theoretical yield) remains.

Analysis (percent by weight): C=45.0 (44.96); H=7.50 (7.49); Sn=30.9 (31.76); F=4.93 (5.08).

EXAMPLE 10

Monododecylfluorotin diethylhexanoate

Dodecanestannonic acid, hydrofluoric acid, and 2-ethylhexanoic acid are combined as in Example 9 in a mol ratio of 1:1:2. A quantitative yield of monododecylfluorotin diethylhexanoate is obtained.

Analysis (percent by weight): C=56.4 (54.69); H=9.30 (9.28); Sn=20.0 (20.03); F=3.10 (3.21).

EXAMPLE 11

Monooctyldifluorotin ethylhexanoate 26.47 g (0.1 mol) of octanestannonic acid, 20 g of 20 percent HF (0.2 mol), and 14.4 g (0.1 mol) of ethylhexanoic acid are heated to boiling in 30 ml of toluene, whereby, with azeotropic removal of water, a clear solution is formed. After removal of the residual toluene, a cream colored residue remains in an amount of 39.62 g (96 percent of theory).

Analysis (Percent by weight): Sn=28.2 (28.76); F=9.12 (9.21).

EXAMPLE 12

Monobutyldifluorotin benzoate 0.1 mol of butanestannonic acid, 0.2 mol of hydrofluoric acid, and 0.1 mol of benzoic acid are reacted with each other as in Example 11. A yellow-brown solid is obtained in 99 percent yield.

Analysis (Percent by weight): C=39.56 (39.44); H=4.50 (4.18); Sn=34.9 (35.46); F=10.9 (11.35).

EXAMPLE 13

Hydrophobizing of Textiles

For hydrophobizing, strips of cotton cloth having a weight of 350 g/m² are saturated in a solution, in white spirit, of either monododecylfluorotin diethylhexanoate or of monooctyldifluorotin ethylhexanoate and are subsequently dried for three days at room temperature.

The water repellant effect is investigated according to AMTCC-Test Method No. 22-1967. As a comparison product, a commercially available silicon impregnating agent is employed.

| Treating Agent | Concentration On Cloth (percent) | Evaluation |
| --- | --- | --- |
| Monododecylfluorotin diethylhexanoate | 0.5 | 100 |
| Monooctyldifluorotin ethylhexanoate | 0.5 | 100 |
| Commercial silicon product | 0.5 | 90 |
| Untreated | — | 0 |

100 = no wetting of the upper test surface
90 = light wetting of the upper test surface at random points
0 = complete wetting of the total upper and lower test surfaces

EXAMPLE 14

Hydrophobizing of Ceramic Material (Concrete)

Concrete cubes four cm on a side were saturated for 24 hours with a 10 percent solution of monobutyldifluorotin acetate in water and dried for three days at 23° C. in an atmosphere with a relative humidity of 50 percent.

Subsequently, the concrete cubes were stored in water for seven days at room temperature and their water uptake was then determined by weighing. The average amount of water absorbed by each cube served as a measure for the hydrophobizing property of the compound.

| Treating Agent | Average Water Uptake After 7 Days (g) |
| --- | --- |
| Monobutyldifluorotin acetate | 0.7 |
| Untreated | 5.5 |

What is claimed is:

1. A monoalkylfluorotin compound of the formula

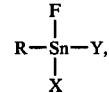

wherein R is alkyl having 1 to 12 carbon atoms, X taken alone is fluorine or carboxylate, Y taken alone is chlorine, carboxylate,

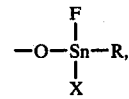

or wherein X and Y, taken together, are oxygen.

2. A monoalkylfluorotin compound as in claim 1 wherein Y is

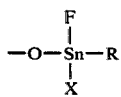

and X is fluorine.

3. A monoalkylfluorotin compound as in claim 2 wherein R is butyl or octyl.

4. A method for making a compound as in claim 1 wherein Y is

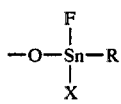

which comprises reacting an alkanestannonic acid with hydrogen fluoride in a mol ratio of at least 1:2 at a temperature from 20° C. to 100° C.

5. A method for making a compound as in claim 1 wherein X is fluorine and Y is carboxylate which comprises reacting a stannoxane of the formula

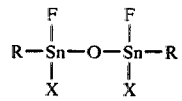

with an excess of a carboxylic acid, YH, at a temperature from 70° C. to 120° C. and removing the water of reaction.

6. A method for making a compound as in claim 1 wherein X and Y, taken together, are oxygen which comprises reacting an alkanestannonic acid with hydrogen fluoride in a mol ratio of 1:1 at a temperature from 20° C. to 100° C.

7. A method for making a compound as in claim 1 wherein X is fluorine and Y is chlorine which comprises reacting an organotin trichloride with an aqueous solution of an alkali metal fluoride in a mol ratio of 1:2 at a temperature from 80° C. to 100° C.

8. A method for making a compound as in claim 1 wherein X is fluorine and Y is carboxylate which comprises reacting an alkanestannonic acid, hydrogen fluoride, and a carboxylic acid in a mol ratio of 1:2:1 at a temperature from 70° C. to 120° C. and removing the water of reaction.

9. A method for making a compound as in claim 1 wherein X and Y are carboxylate which comprises reacting an alkanestannonic acid, hydrogen fluoride, and a carboxylic acid in a mol ratio of 1:1:2 at a temperature from 70° C. to 120° C. and removing the water of reaction.

* * * * *